United States Patent
Hopes et al.

(10) Patent No.: US 7,973,178 B2
(45) Date of Patent: *Jul. 5, 2011

(54) CHEMICAL PROCESS FOR THE PREPARATION OF AN AMIDO-PHENOXYBENZOIC ACID COMPOUND

(75) Inventors: Phillip Anthony Hopes, Bristol (GB); Jeremy Stephen Parker, Bristol (GB); Bharti Patel, Bristol (GB); Matthew James Welham, Bristol (GB)

(73) Assignee: AstraZeneca AB, Sodertalje (SE)

( * ) Notice: Subject to any disclaimer, the term of this patent is extended or adjusted under 35 U.S.C. 154(b) by 317 days.

This patent is subject to a terminal disclaimer.

(21) Appl. No.: 12/095,101

(22) PCT Filed: Nov. 27, 2006

(86) PCT No.: PCT/GB2006/004399
§ 371 (c)(1),
(2), (4) Date: May 27, 2008

(87) PCT Pub. No.: WO2007/060448
PCT Pub. Date: May 31, 2007

(65) Prior Publication Data
US 2008/0300412 A1   Dec. 4, 2008

Related U.S. Application Data

(60) Provisional application No. 60/740,042, filed on Nov. 28, 2005.

(51) Int. Cl.
*C07D 205/00* (2006.01)
(52) U.S. Cl. ........................................................ 548/950
(58) Field of Classification Search .................... 548/950
See application file for complete search history.

(56) References Cited

U.S. PATENT DOCUMENTS

| | | |
|---|---|---|
| 2,750,393 A | 6/1956 | Elpern |
| 2,967,194 A | 1/1961 | Hauptschein |
| 3,917,625 A | 11/1975 | Lee et al. |
| 3,950,351 A | 4/1976 | Rossignol et al. |
| 4,009,174 A | 2/1977 | Cluzan et al. |
| 4,105,785 A | 8/1978 | Mauvernay et al. |
| 4,146,631 A | 3/1979 | Ford et al. |
| 4,434,170 A | 2/1984 | Dostert et al. |
| 4,474,792 A | 10/1984 | Erickson |
| 4,634,783 A | 1/1987 | Fujii et al. |
| 4,966,891 A | 10/1990 | Fujiu et al. |
| 5,258,407 A | 11/1993 | Washburn et al. |
| 5,273,986 A | 12/1993 | Holland et al. |
| 5,399,702 A | 3/1995 | Holland et al. |
| 5,466,715 A | 11/1995 | Washburn et al. |
| 5,510,478 A | 4/1996 | Sabb |
| 5,661,153 A | 8/1997 | Isobe et al. |
| 5,672,750 A | 9/1997 | Perry |
| 5,712,270 A | 1/1998 | Sabb |
| 5,849,735 A | 12/1998 | Albright et al. |
| 6,110,945 A | 8/2000 | Head et al. |
| 6,197,798 B1 | 3/2001 | Fink et al. |
| 6,200,995 B1 | 3/2001 | De la Brouse-Elwood et al. |
| 6,207,693 B1 | 3/2001 | Setoi et al. |
| 6,214,878 B1 | 4/2001 | Bernardon et al. |
| 6,242,474 B1 | 6/2001 | Yamasaki et al. |
| 6,255,335 B1 | 7/2001 | Himmler et al. |
| 6,316,482 B1 | 11/2001 | Setoi et al. |
| 6,320,050 B1 | 11/2001 | Bizzarro et al. |
| 6,348,474 B1 | 2/2002 | Kayakiri et al. |
| 6,369,229 B1 | 4/2002 | Head et al. |
| 6,376,515 B2 | 4/2002 | Zhu et al. |
| 6,388,071 B2 | 5/2002 | Mahaney |
| 6,448,399 B1 | 9/2002 | Corbett et al. |
| 6,486,349 B1 | 11/2002 | Flitter et al. |
| 6,528,543 B1 | 3/2003 | Bizzarro et al. |
| 6,545,155 B2 | 4/2003 | Corbett et al. |
| 6,610,846 B1 | 8/2003 | Bizzarro et al. |
| 6,613,942 B1 | 9/2003 | Ling et al. |
| 6,989,402 B1 * | 1/2006 | Hangeland et al. ........... 514/563 |
| 7,132,546 B2 | 11/2006 | Kato et al. |
| 7,199,140 B2 | 4/2007 | Hayter et al. |
| 7,230,108 B2 | 6/2007 | Hargreaves et al. |
| 7,700,640 B2 * | 4/2010 | Cornwall et al. ............. 514/407 |

(Continued)

FOREIGN PATENT DOCUMENTS
CA   2605738   11/2006
(Continued)

OTHER PUBLICATIONS

Berl et al. "Induced fit selection of a barbiturate receptor from a dynamic structural and conformational/ configurational library" European J. Org. Chem. (11):3089-3094 (1999).

(Continued)

*Primary Examiner* — Rei-tsang Shiao
(74) *Attorney, Agent, or Firm* — Morgan Lewis & Bockius LLP

(57) ABSTRACT

A process for making a compound of formula (I),

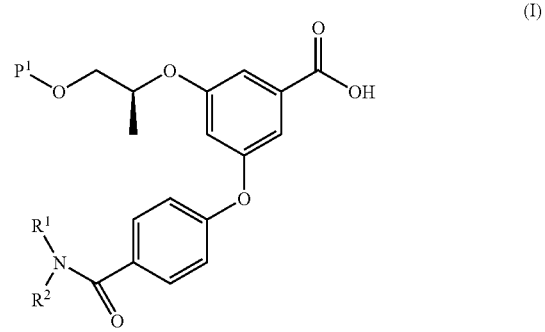

which is useful as an intermediate to compounds which activate glucokinase, is described, (wherein $P^1$, $R^1$ and $R^2$ are as defined in the description).

12 Claims, No Drawings

U.S. PATENT DOCUMENTS

| | | |
|---|---|---|
| 2001/0027200 A1 | 10/2001 | De la Brouse-Elwood et al. |
| 2002/0002183 A1 | 1/2002 | Zhu et al. |
| 2002/0095044 A1 | 7/2002 | Jagtap et al. |
| 2003/0162690 A1 | 8/2003 | Zhu et al. |
| 2004/0014968 A1 | 1/2004 | Bizzarro et al. |
| 2004/0077555 A1 | 4/2004 | Ishihara et al. |
| 2005/0080106 A1 | 4/2005 | Boyd et al. |
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0167053 A1 | 7/2006 | Iino et al. |
| 2006/0258728 A1 | 11/2006 | Tani et al. |
| 2007/0078168 A1 | 4/2007 | Caulkett |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1600442 | 11/2005 |
| EP | 1702919 | 9/2006 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |
| WO | WO 02/051831 | 7/2002 |
| WO | WO 02/064545 | 8/2002 |
| WO | WO 02/079145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/081001 | 9/2004 |

| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 20085/054233 | 6/2005 |
| WO | WOL 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/031739 | 3/2007 |
| WO | WO 2007/053657 | 5/2007 |
| WO | WO 2008/050101 | 5/2008 |
| WO | WO 2008/050117 | 5/2008 |
| WO | WO 2008/075073 | 6/2008 |

OTHER PUBLICATIONS

Berl et al. "Template-induced and molecular recognition directed hierarchical generation of supramolecular assemblies from molecular strands" Chem. Eur. J. 6(11):1938-1946 (2000).
Bonina et al. "Synthesis and pharmacologic activity of 2-arylethenylthiazol-4-acetic and 4-carboxylic acids" II Farmaco 40(11):875-884 (1985).
Boucherle et al. "Recherches dans la serie des cetones polyphenoliques IV. Thiazoles" Chimica. Therapeutica. 3(5):360-363 (1968) (Translation enclosed).
Bowden et al. "Structure-activity relations. Part 10. Metal-ion-complexation studies of a series of substituted benzamidotetrazoles" J. Chem. Research (Synopses) 11:304 (1991).
Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).
Brenner et al. "Imino-bridged heterocycles. VII. (1) N-aminobenzocycloheptapyridinimines" J. Heterocyclic Chem. 23:1331-1332 (1986).
Brocklehurst et al. "Stimulation of hepatocyte glucose metabolism by novel small molecule glucokinase activators" Diabetes 53:535-541 (2004).
Caro et al. "Liver glucokinase: Decreased activity in patients with type II diabetes" Horm. Metab. Res. 27(1):19-22 (1995).
Carroll et al. "The in vitro characterisation of a novel Glucokinase activator" Stress, Signalling and Control, Biochemical Society Meeting 679, University of Essex, UK (Jul. 2-4, 2003).
Caulfield et al. "The first potent and selective inhibitors of the glycine transporter type 2" J. Med. Chem. 44(17):2679-2682 (2001).
Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).
Chemical Abstracts Service, Columbus, Ohio, US: CAS Registry No. 438028-05-8 (Nov. 15, 2001); CAS Registry No. 438024-90-9 (Nov. 15, 2001), [XP002272448].
Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].
Chemical Abstracts Service, Columbus, Ohio, US: CAS Registry No. 354767-51-4 (Sep. 5, 2001).
Chemical Abstracts Service, Columbus, Ohio, US: CAS Registry No. 354767-66-1 (Sep. 5, 2001).
Christesen et al. "The second activating glucokinase mutation (A456V): Implications for glucose homeostasis and diabetes therapy" Diabetes 51(4):1240-1246 (2002).
Ciaceri et al. "Analgesic, antipyretic and anti-inflammatory action of some new acids of the phenylethylenethiazole series" Minerva Medica 63(42):2409-2413 (1972).
Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).
Coghlan "Small molecule Glucokinase Activators (GKAs) as novel anti-diabetic agents" CIDEM seminar (May 2005).
Coghlan "Small molecule Glucokinase Activators (GKAs) as novel anti-diabetic agents" Society for Medicines Research Seminar (Jun. 2004).
Coope et al. "Predictive blood glucose lowering efficacy by Glucokinase activators in high fat fed female Zucker rats" British Journal of Pharmacology 149(3):328-335 (2006).
Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).
Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).
Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).
De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).
DeFronzo et al. "The triumvirate: β-cell, muscle, liver. A collusion responsible for NIDDM" Diabetes 37:667-687 (1988).
DeJohn et al. "Functionalization of Substituted 2(1H)- and 4(1H)-Pyridones. III. The preparation of substituted 6-vinyl-1,2-dihydro-2-oxo- and 1,4-dihydro-4-oxo-3-pyridinecarboxylic acids through the chemistry of pyridone dianions" J. Heterocyclic Chem. 20(5):1295-1302 (1983).
Desai et al. "Phenotypic correction of diabetic mice by adenovirus-mediated glucokinase expression" Diabetes 50:2287-2295 (2001).
Edmont et al. "Synthesis and evaluation of quinoline carboxyguanidines as antidiabetic agents" Bioorg. Med. Chem. Lett. 10(16):1831-1834 (2000).
Elpern et al. "Iodinated Benzamidotetrazoles" J. Org. Chem. 22: 1686 (1957).
Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" Abstract No. 0108-OR, 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—A glucokinase activator" Abstract No. 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution"" Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methylmorpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract No. 0377-OR, 67th Annual Scientific Sessions, American Diabetes Association, Chicago, IL (Jun. 22-26, 2007).

Leighton et al. "Small molecule glucokinase activators as novel anti-diabetic agents" Biochemical Society Transactions 33(Part 2):371-374 (2005).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt 2):R1223-R1231 (1999).

Levin et al. "Differential effects of diet and obesity on high and low affinity sulfonylurea binding sites in the rat brain" Brain Research 739(1-2):293-300 (1996).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al. "Research on cyanide dyes 11. 7,7'-Dimethylthiacarbocyanines" Zhurnal Obshchei Khimii 27:3097-3107 (1957) (Translation enclosed).

Lynch et al. "Localization of glucokinase gene expression in the rat brain" Diabetes 49(5):693-700 (2000).

Mastafanova et al. "Features of the catalytic reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).

Mastafanova et al. "Synthesis and study of the antihypertensive activity of substituted N-acetylmercaptopropionyl-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial receptors: systematic studies towards recognition motifs for carbohydrates" Chem. Eur. J. 7(3):664-670 (2001).

Mazik et al. "Molecular recognition of carbohydrates by artificial polypyridine and polypyrimidine receptors" Anaewandte Chemie International Edition 39(3):551-554 (2000).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Lett. 16(10):2705-2709 (May 15, 2006) Epub Feb. 28, 2006.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al "Chiral amplification in supramolecular stacks" Polymer Preprints 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11):1882-1887 (2001).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328-7336 (1998).

Palmans "Extended-core discotic liquid crystals based on the intramolecular H-bonding in N-acylated 2,2'-bipyridine-3,3'-diamine moieties" Chem. Eur J. 3(2):300-307 (1997).

Plieninger et al. "Synthesis of 7,8-dihydro-5,6-benzoquinoline-(3)-carboxylic acid" Chemische Berichte 87:882-887 (1954) (Translation enclosed).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).

Qian-Cutrone et al. "Glucolipsin A and B, two new glucokinase activators produced by *Streptomyces purpurogenisclerotiucus* and *Nocardia vaccinii*" Journal of Antibiotics (Tokyo), 52(3):245-255 (1999).

Rivalle et al. "2,3 Disubstituted furans and pyrroles—XVIII: Synthesis and rearrangement of 4H-dihydro-9,10 benzo[4,5]cyclohepta[1,2-b]furannones-4" Tetrahedron 32(7):829-834 (1976).

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

Rogers et al. "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497.2:365-377 (1996).

Schuit et al. "Glucose sensing in pancreatic β-Cells. A model for the study of other glucose-regulated cells in gut, pancreas, and hypothalamus" Diabetes 50:1-11 (2001).

Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).

Seoane et al. "Glucokinase overexpression restores glucose utilization and storage in cultured hepatocytes from male Zucker diabetic fatty rats" J Biol Chem. 274(45):31833-31838 (1999).

Shiota et al. "Glucokinase gene locus transgenic mice are resistant to the development of obesity-induced type 2 diabetes" Diabetes 50(3):622-629 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7): 515-523 (1997).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas" J Am. Chem. Soc. 124(49):14759-14769 (2002).

Vanderstelt et al. "Synthesis and pharmacological properties of some derivatives of 5H-benzo[4,5] cyclohepta[1,2-b] pyridine and of 11H-benzo[5,6] cyclohepta[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulation of hepatocyte glucose metabolism by pharmacological agents" Diabetologia, 47 Supp 1, A 214, 589 (2004)

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007) and Diabetes vol. 56 (Supplement 1) 1482-P (2007).

Yakushijin et al. "Intramolecular ring formation of phenyl azide and furan" Heterocycles 12(8):1021-1026 (1979).

Yakushijin et al. "Intramolecular ring formation of phenyl azide and furan moieties" Chem. Pharm. Bull. 30(1):140-151 (1982).

Yang et al. "Hypothalamic glucose sensor: similarities to and differences from pancreatic beta-cell mechanisms" Diabetes 48(9):1763-1772 (1999).

Yoshina et al. "Studies of heterocyclic compounds. II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2-(2-furyl)vinylbenzenes and 2-(2-furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

Alvarez et al. "Evidence that glucokinase regulatory protein is expressed and interacts with glucokinase in rat brain" J. Neurochem. 80(1):45-53 (2002).

Alvarez et al. "Expression of the glucagon-like peptide-1 receptor gene in rat brain" J. Neurochem. 66(3):920-927 (1996).

Anderson et al "Pyridopyrimidines. 6. Nucleophilic substitutions in the pyrido[2,3-d]pyrimidine series" J. Org. Chem. 42(6):993-996 (1977).

Ando et al. "Fluoride salts on alumina as reagents for alkylation of phenols and alcohols" Bull. Chem. Soc. Jpn. 55(8):2504-2507 (1982).

Atwell et al. "Potential antitumor agents. VI. Bisquaternary salts" J. Med. Chem. 11(2):295-300 (1968).

Baker et al. "Structure and synthesis of Pallescansin E utilising a modified Wadsworth-Emmons reaction" J. Chem. Soc., Perkin Trans. 1, 12:3087-3091 (1981).

Baker et al. "Synthesis of Pallescensin-E: Use of crown ether in the Wadsworth procedure for olefin formation" Tetrahedron Letters 22:161-162 (1981).

Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).

Beilstein Registry No. 6511458 (Apr. 18, 1994) [XP002272206].

Bell et al. "Glucokinase mutations, insulin secretion, and diabetes mellitus" Annu. Rev. Physiol. 58:171-186 (1996).

Beller et al. "Photochemical synthesis of benzo[f]quinolines" J Org Chem. 42(22):3514-3518 (1977).

Coghlan et al., "Glucokinase activators in diabetes management" Expert Opin. Investig. Drugs 17(2):145-167 (2008).

Leighton, "Pre-clinical disease models—challenges and success stories"44th Drug Information Association Annual Meeting, Boston, MA, US (2008).

Lith, "Evaluation of the effects on whole body glucose metabolism after single doses of X2000—A glucose lowering agent" Poster presentation, Master thesis in Pharmaceutical Bioscience, Goteborgs University (2008).

Ralph et al. "Glucose Modulation of Glucokinase Activation by Small Molecules" Biochemistry 47(17):5028-5036 (2008).

Sarabu et al., "Glucokinase activators as new type 2 diabetes therapeutic agents" Expert Opinion on Therapeutic Patents 18(7):759-768 (2008).

Shorvon, "Pyrrolidone derivatives" Lancet 358(9296):1885-1892 (2001).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

West, Anthony R., "Solid State Chemistry and its Applications" Wiley, New York, pp. 358 and 365 (1988).

Wolff, Manfred E. "Burger's Medicinal Chemistry", 5th Edition, Part I, John Wiley & Sons, pp. 975-977 (1995).

\* cited by examiner

CHEMICAL PROCESS FOR THE PREPARATION OF AN AMIDO-PHENOXYBENZOIC ACID COMPOUND

RELATED APPLICATIONS

The present application is a U.S. National Phase Application of International Application No. PCT/GB2006/004399 (filed Nov. 27, 2006) which claims the benefit of U.S. Provisional Application No. 60/740,042 (filed Nov. 28, 2005), both of which are hereby incorporated by reference in their entirety.

This invention relates to an improved chemical process for making compounds which are useful in the treatment or prevention of a disease or medical condition mediated through glucokinase (GLK or GK), leading to a decreased glucose threshold for insulin secretion. Such compounds are predicted to lower blood glucose by increasing hepatic glucose uptake. Such compounds may have utility in the treatment of Type 2 diabetes and obesity. The invention is also related to intermediates useful in the improved chemical process.

In our applications (WO2005/080359, WO2005/080360, WO 2005/121110 (PCT/GB2005/002166), WO 2006/040529 (PCT/GB2005/003890) and WO 2006/040528 (PCT/GB2005/003888)) we have described compounds which are useful as GLK activators, which are of general chemical formula (A).

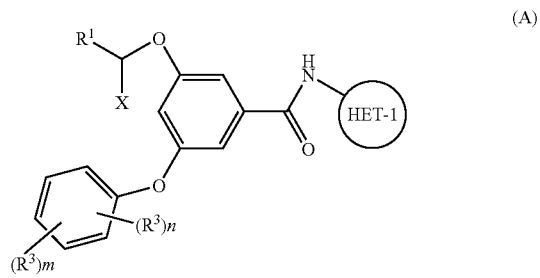
(A)

wherein for example $R^1$ is hydroxymethyl, methoxymethyl or methyl;

X is methyl or ethyl;

$R^2$ is selected from —C(O)$NR^4R^5$, —$SO_2NR^4R^5$, —S(O)$_pR^4$ and HET-2;

HET-1 is an optionally substituted 5- or 6-membered, C-linked heteroaryl ring containing a nitrogen atom in the 2-position;

HET-2 is an optionally substituted 4-, 5- or 6-membered, C- or N-linked heterocyclyl ring containing 1, 2, 3 or 4 heteroatoms;

$R^3$ is selected from halo, fluoromethyl, difluoromethyl, trifluoromethyl, methyl, methoxy and cyano;

$R^4$ is selected from hydrogen, (1-4C)alkyl [optionally substituted], (3-6C)cycloalkyl (optionally substituted) and HET-2;

$R^5$ is hydrogen or (1-4C)alkyl;

or $R^4$ and $R^5$ together with the nitrogen atom to which they are attached may form a heterocyclyl ring system;

m is 0 or 1;

n is 0, 1 or 2;

provided that when m is 0, then n is 1 or 2; or a salt, pro-drug or solvate thereof.

The compounds of formula (A) are N-heterocyclyl-aryl amides, wherein the aryl ring is 3,5-disubstituted by a substituted alkyl ether and an aryloxy substituent. These compounds have for example been synthesised using reaction sequences such as those illustrated in Schemes 1 and 2 below:

Scheme 1

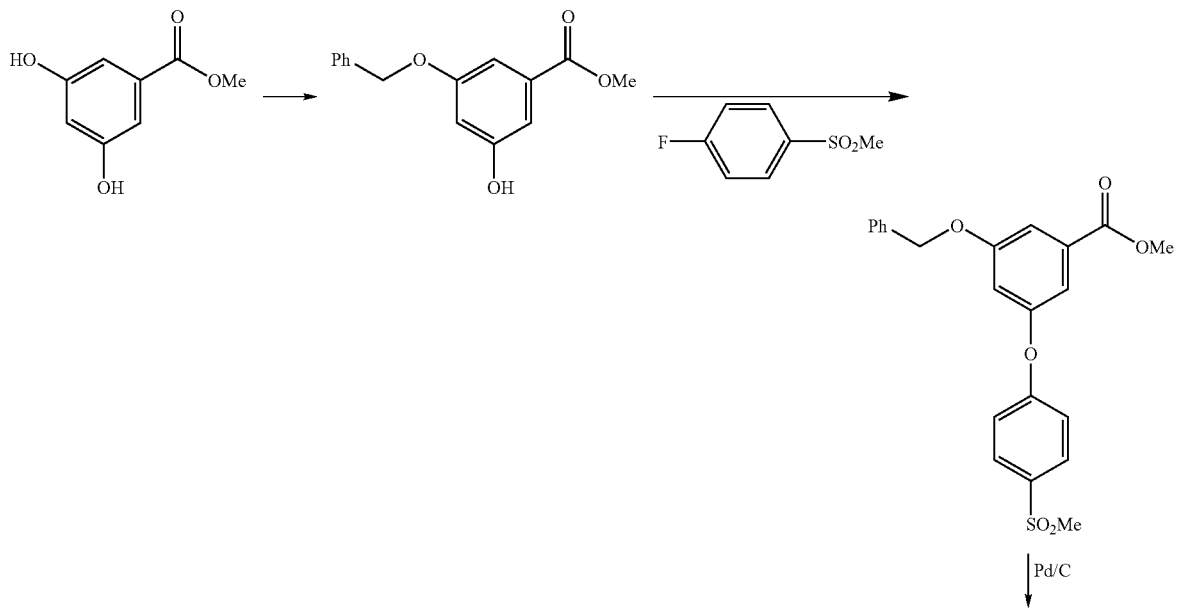

3 4
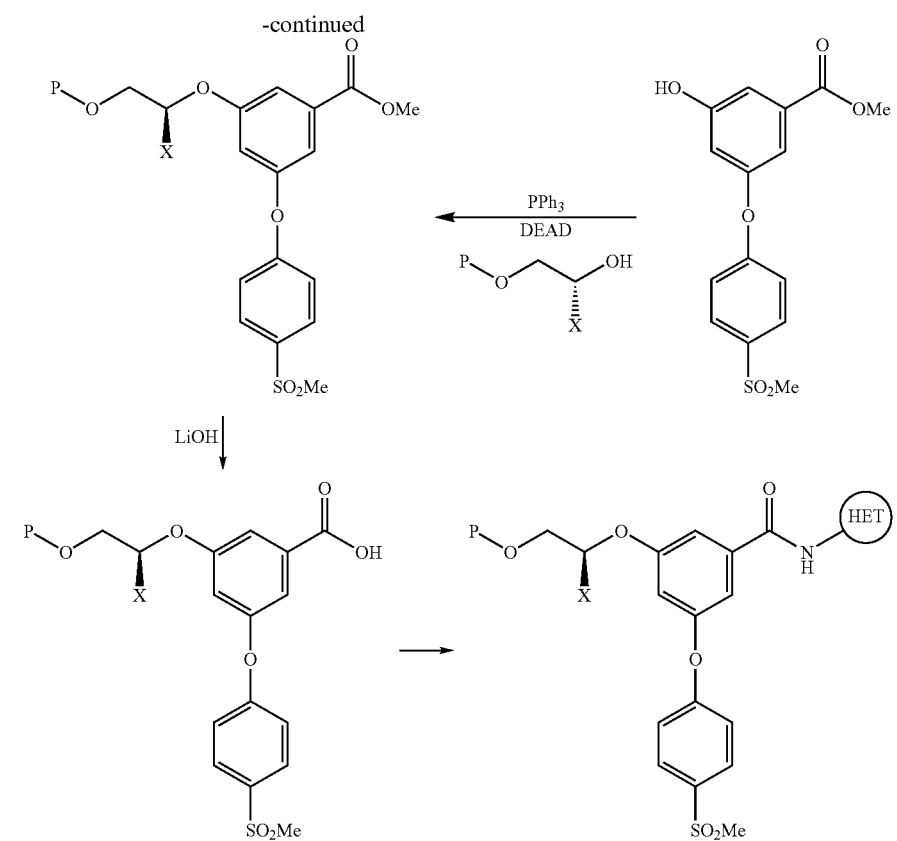
where X is as defined in Formula (A), P is methyl or a protecting group such as a trialkylsilyl group.
Scheme 2
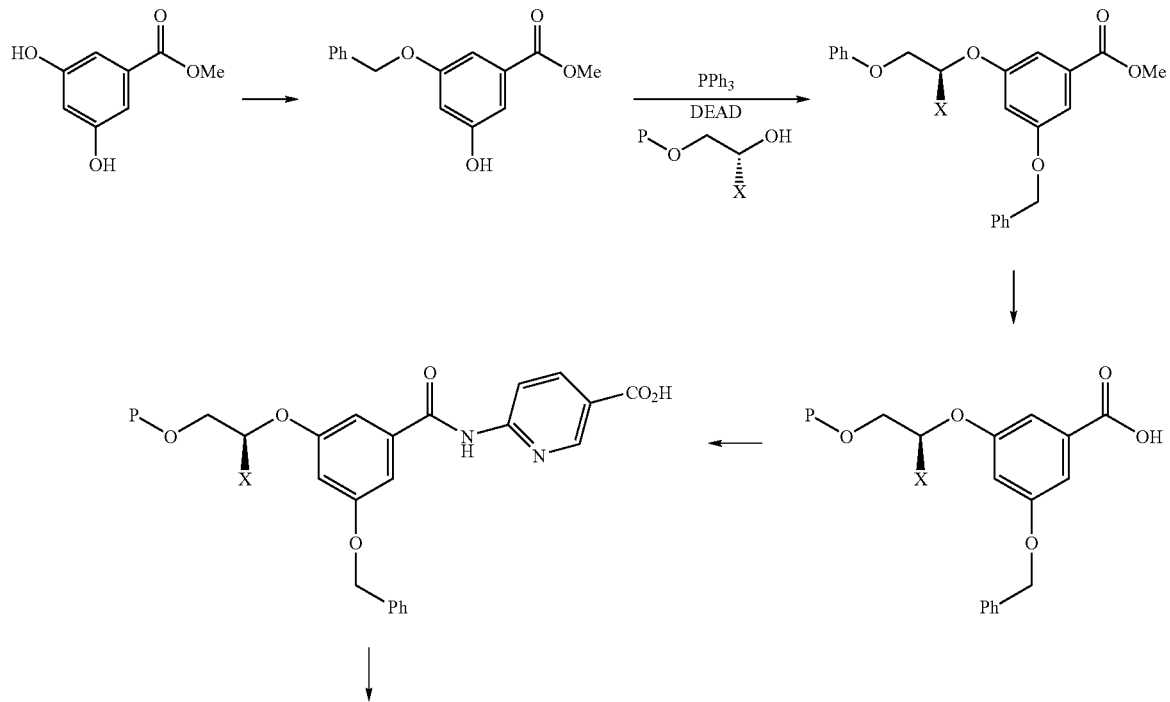

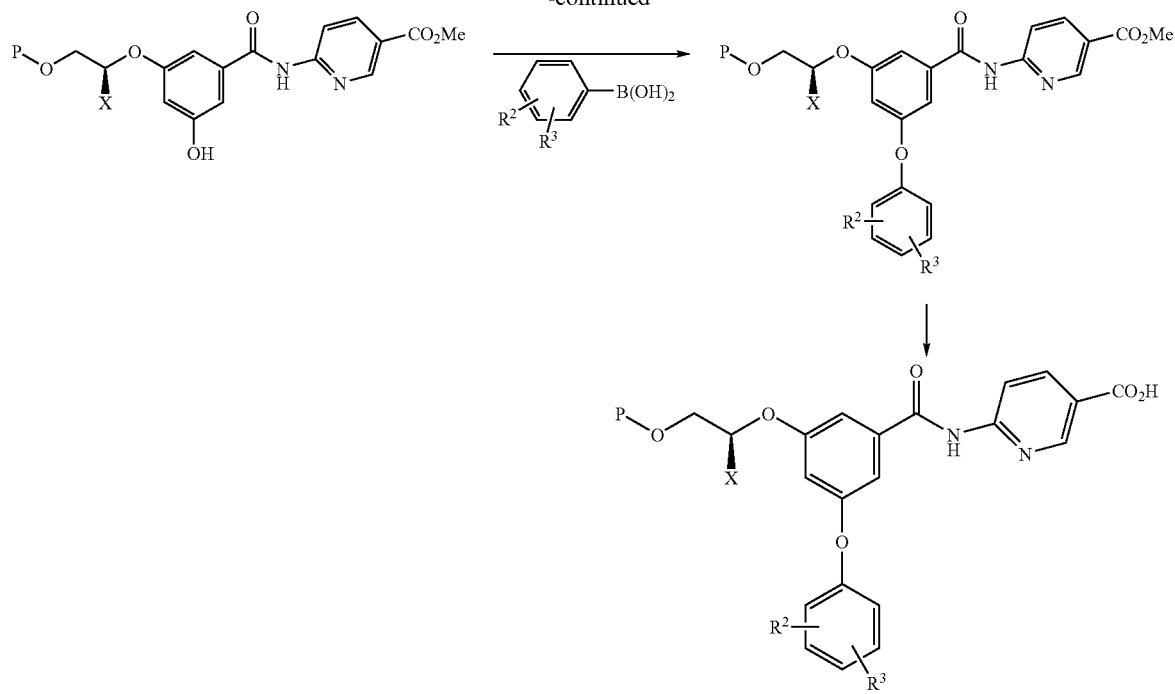

The starting material for both of these synthetic routes is methyl(3,5-dihydroxy)benzoate. The order of attaching the various substituents around the phenyl ring has varied, but in both routes illustrated, it has been necessary to use protecting groups (benzyl in Schemes 1 and 2) during the synthetic sequence in order to differentiate between the two hydroxy groups in the starting material. This inevitably introduces extra synthetic steps with the consequent implications for increased cost per unit weight of final product and increased waste and environmental impact, if the product were to be manufactured on significant scale.

Concurrently, compounds with a similar general formula have been published (WO 2004/076420). A route used to these compounds is illustrated in Scheme 3.

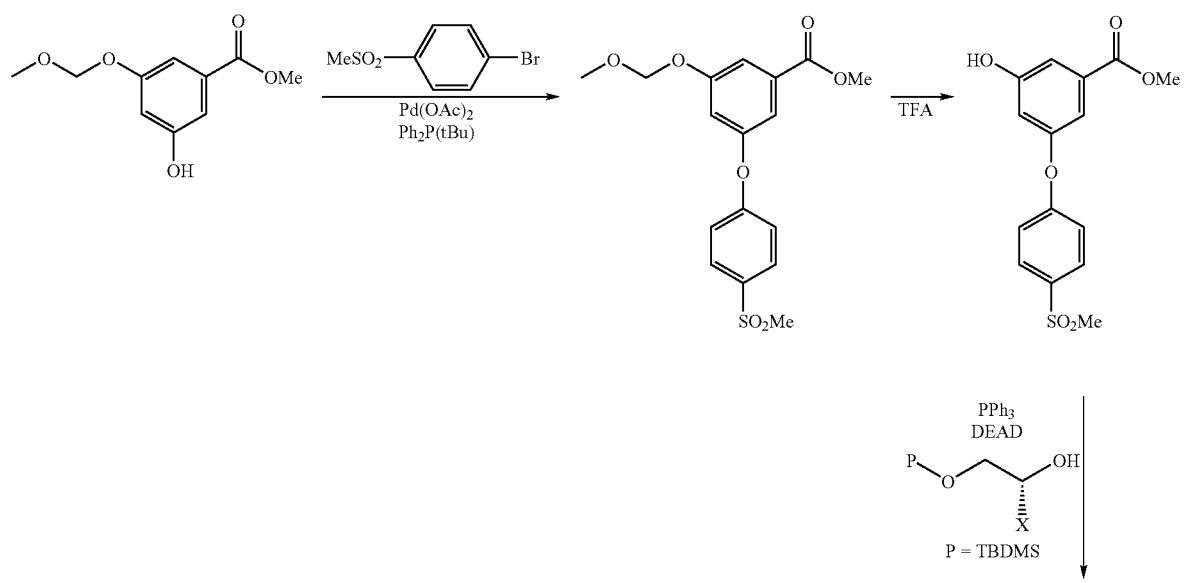

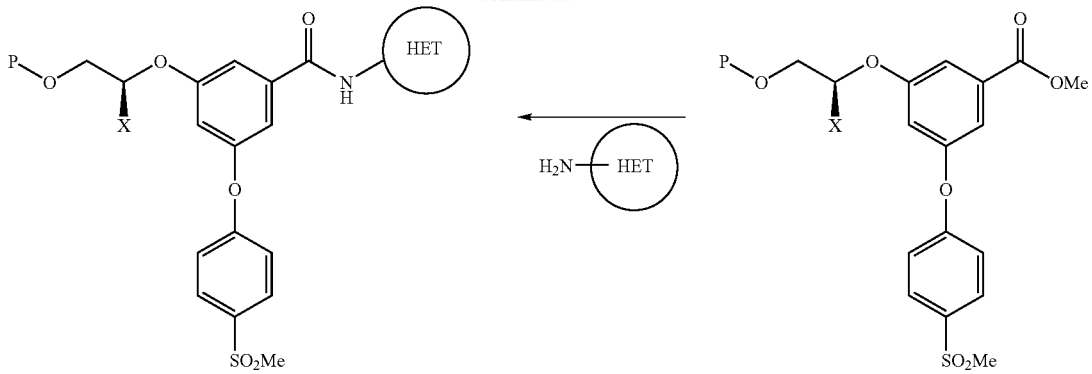

However, as shown above, a methoxymethyl protecting group is still utilised in this route.

In order for such compounds to be useful commercially, there is a need to develop one or more short, efficient synthetic routes. In our co-pending PCT application PCT/GB2005/003882 we have described routes to the above compounds starting from dihalophenyl derivatives, which were exemplified, inter alia, according to the scheme below:

Scheme 4

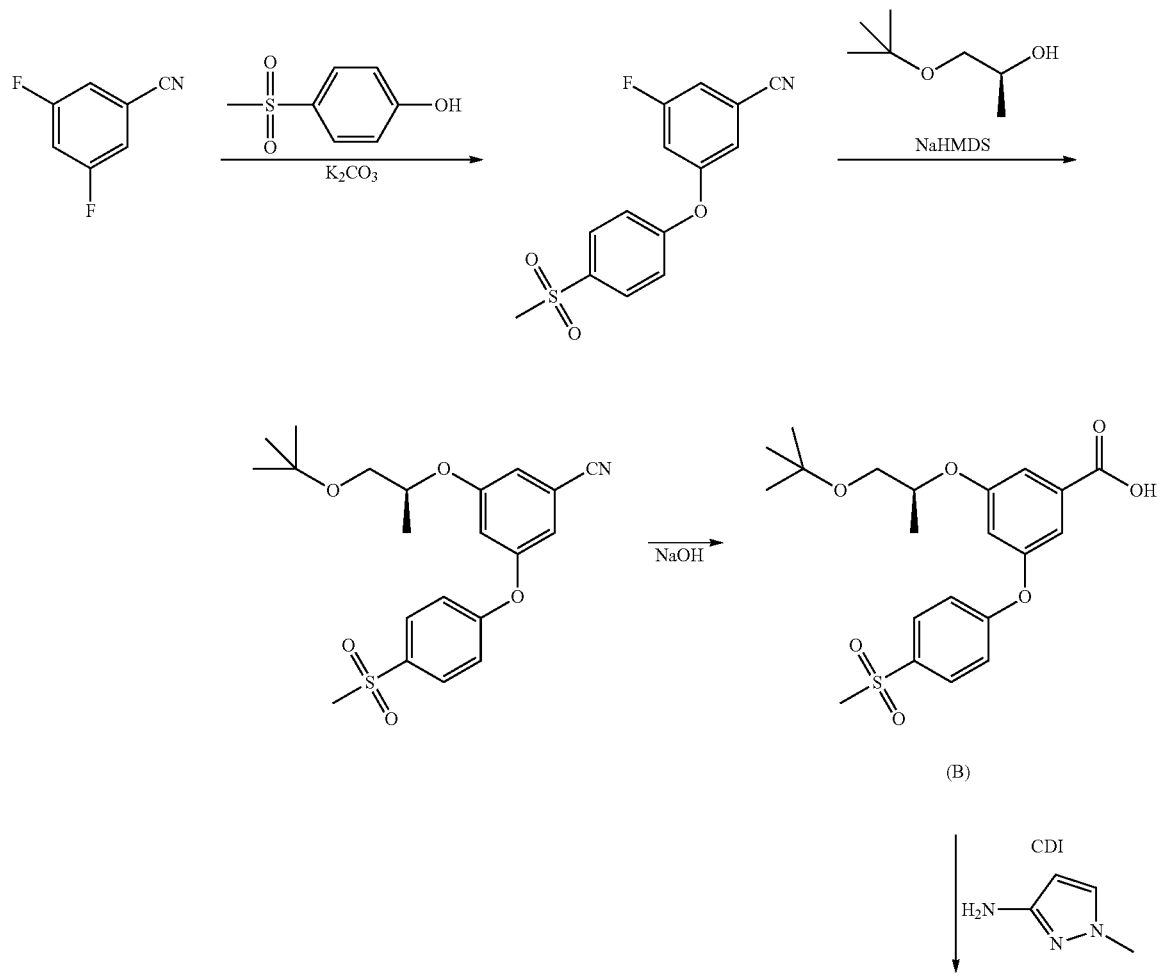

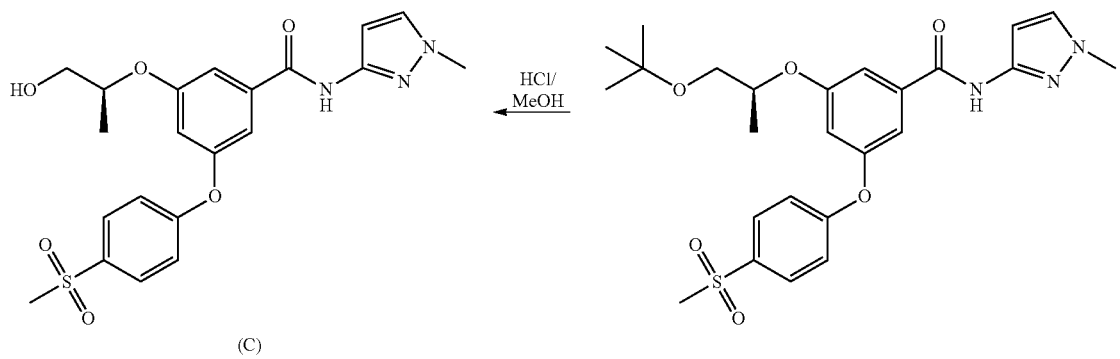

(C)

A key intermediate in this process is the benzoic acid derivative (B). Use of this intermediate provides rapid access to a number of heterocyclic amide analogues (such as compound (C)) by formation of the heterocyclic amide bond (illustrated above by the heterocycle being methylpyrazole).

Synthesis of intermediates of analogous structure to (B), where the methylsulfonyl group has been replaced by an amide, provides further challenges. For example, the conversion of the nitrile group to the carboxylic acid group of (B) using reagents such as sodium hydroxide may cause at least partial hydrolysis of the amide $R^1R^2N$—CO— as shown below:

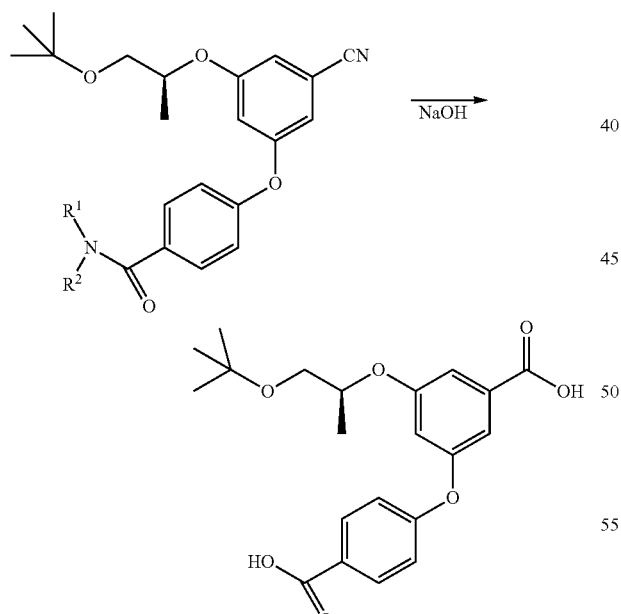

Although the conversion of the nitrile to the desired carboxylic acid derivative, such as (B), may work to some useful degree, it would be advantageous to develop routes to compounds analogous to compound (B) which can tolerate the presence of sensitive substituents such as amides, to give high yields of the required carboxy intermediate, on a significant scale, for further elaboration to the final product (D) (wherein HET-1 is an optionally substituted 5- or 6-membered, C-linked heteroaryl ring containing a nitrogen atom in the 2-position):

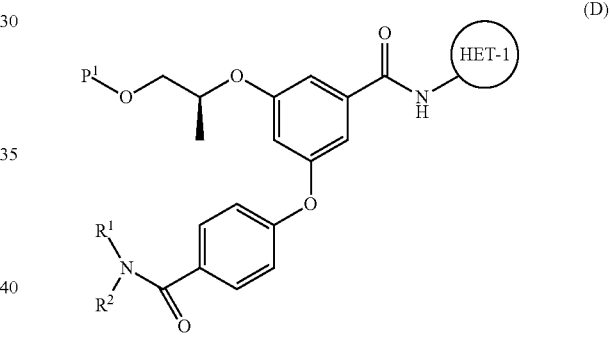

According to a first aspect of the invention, there is provided a process for making a compound of formula (I),

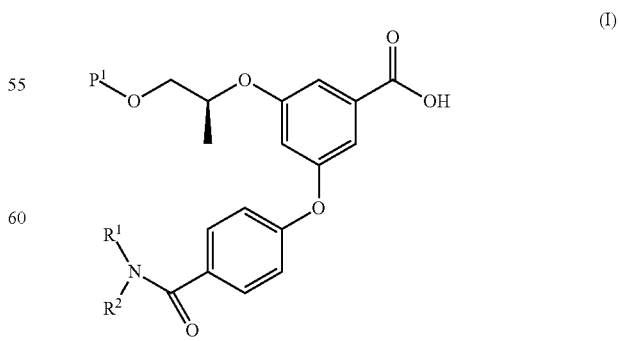

said process comprising either:
a) hydrolysis of an ester of formula (II) (wherein R is (1-4C) alkyl);

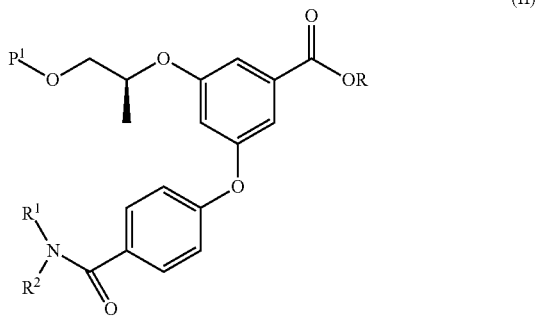

(II)

or
b) reaction of a halo derivative of formula (III) (wherein Hal represents a halogen) with a compound of formula (IV);

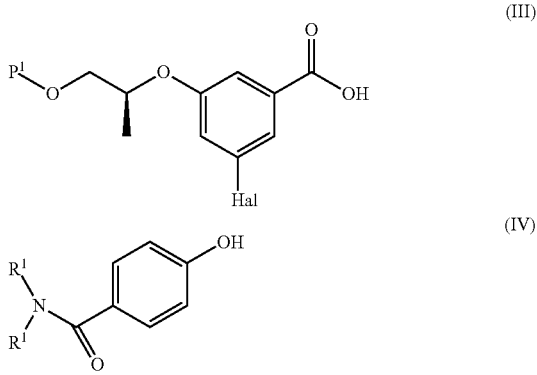

(III)

(IV)

wherein in compounds of formula (I) to (IV), $R^1$ and $R^2$ are independently selected from hydrogen and (1-6C)alkyl, or $R^1$ and $R^2$ together with the nitrogen to which they are attached form a 4- to 7-membered heterocyclic ring, said ring optionally containing 1 further heteroatom selected from O, N and S; and
$P^1$ is hydrogen or a hydroxy protecting group.

In one aspect of the invention, the compound of formula (I) is made by process a).

In another aspect of the invention, the compound of formula (I) is made by process b).

Suitable conditions for process a) are hydrolysis under mild basic conditions such as the use of sodium hydroxide in tetrahydrofuran. Further suitable conditions include sodium hydroxide in water/methanol at room temperature (Tetrahedron Letters, 46(25), 4311-4313; 2005, and Angewandte Chemie, International Edition, 44(1), 72-75; 2004); and lithium hydroxide in THF/water/methanol at room temperature (Journal of the American Chemical Society, 127(15), 5540-5551; 2005).

Suitable conditions for process b) are those known to be suitable for Ullman reactions. For example see K Kunz, U Scholz, D Ganzer, *Synlett*, 2003, 2428-2439, G Mann, C Incarvito, A L Rheingold & J Hartwig, *J. Am. Chem. Soc.*, 1999, 121, 3224-3225 and A Aranyos, D W Old, A Kiyomori, J P Wolfe, J P Sadighi & S L Buckwald, *J. Am. Chem. Soc.*, 1999, 121, 4369-4378.

Generally, suitable conditions for process b) are use of a high boiling solvent (for example toluene, 1,4-dioxane or DMSO or, for example benzonitrile, dimethylformamide, N-methylpyrrolidone (NMP) or N,N-dimethylpropyleneurea (DMPU)); using a copper or palladium catalyst (for example copper, copper (I) chloride, copper (I) bromide, copper (I) iodide, copper (II) chloride, copper (II) bromide, copper (II) iodide, copper (II) oxide, palladium (II) acetate or bisdibenzylideneacetone palladium (0), or for example copper (I) oxide); a ligand for the catalyst (for example 1,10-phenanthronine, neocuprine, a 1,3-diketone (such as 2,2,6,6-tetramethylheptane-3,5-dione), racemic-2-(di-t-butylphsophino)-1, 1'-binaphthyl, 2-(di-t-butylphosphino)biphenyl or 1,1'-bis (di-t-butylphosphino)ferrocene; or for example a ligand selected from 8-quinolinol, 1,10-phenanthraline, salicaldioxime, 2,2,6,6-tetramethylheptane-3,5-dione and N,N-dimethylglycine, in particular selected from 2,2,6,6-tetramethylheptane-3,5-dione and N,N-dimethylglycine); and a base (for example inorganic bases such as potassium carbonate, cesium carbonate and organic bases such as sodium tert-butoxide) to deprotonate the phenol.

For example process b) may be conducted in NMP or benzonitrile, using copper (I) iodide or copper (I) oxide as catalyst, 2,2,6,6-tetramethylheptane-3,5-dione (or N,N-dimethylglycine, but particularly 2,2,6,6-tetramethylheptane-3, 5-dione (TMHD)) as ligand and cesium carbonate as base. It is advantageous to use cesium carbonate with a high surface area and carry out the reaction with vigorous stirring. In another aspect, process b) is carried out in NMP, with copper (I) iodide, TMHD and cesium carbonate.

Therefore in another aspect of the invention there is provided a process for making a compound of formula (I),

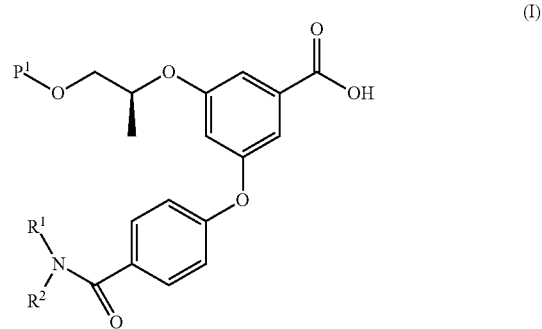

(I)

said process comprising
reaction of a halo derivative of formula (III) (wherein Hal represents a halogen) with a compound of formula (IV);

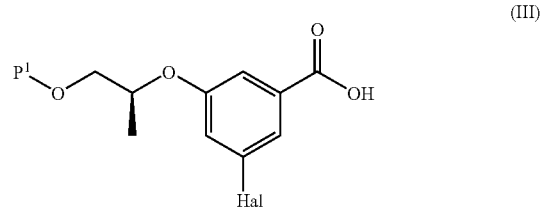

(III)

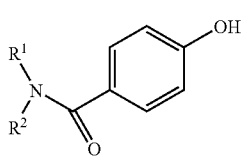
(IV)

in the presence of a catalyst, a ligand for said catalyst and a base,
wherein in compounds of formula (I) to (IV), $R^1$ and $R^2$ are independently selected from hydrogen and (1-6C)alkyl, or $R^1$ and $R^2$ together with the nitrogen to which they are attached form a 4- to 7-membered heterocyclic ring, said ring optionally containing 1 further heteroatom selected from O, N and S; and
$P^1$ is hydrogen or a hydroxy protecting group.

In one aspect, $P^1$ is a hydroxy protecting group.

Suitable values for hydroxy protecting groups $P^1$ are any of those known in the art for protecting primary alcohols (see for example "Protective groups in Organic Chemistry" $3^{nd}$ Edition, T W Greene and PGM Wuts, 1999).

Further suitable values for hydroxy protecting groups $P^1$ are t-butyl, benzyl, trityl (triphenylmethyl) and tetrahydropyran-2-yl; such that the preferred side chains on compounds of formula (I)-(III) are:

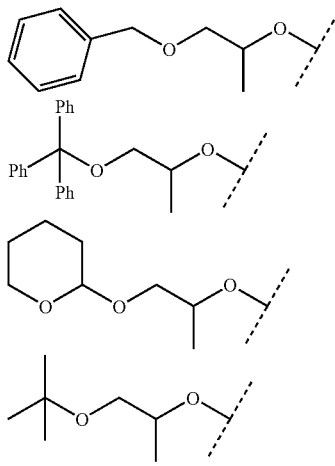

A further suitable protecting group is an allyl ether.
In one aspect, tert-butyl ether:

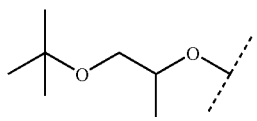

is a preferred protecting group.

In another aspect, $P^1$ is hydrogen.

These protecting groups may be removed at a convenient moment in the subsequent synthetic sequence by methods known in the art. For example, a benzyl group may be removed by hydrogenation. A trityl group or a tert-butyl group may be removed by treatment with acid. Suitable acids or acidic conditions for removal of a tert-butyl group are, for example, treatment with hydrochloric acid in methanol, or treatment with amberlyst resin, or treatment with formic acid.

Compounds of formula (II) may be made as illustrated in Scheme 5 (wherein $P^1$ is tert-butyl).

Scheme 5

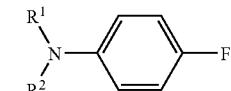
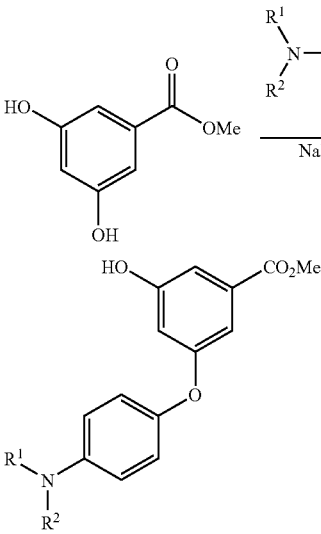
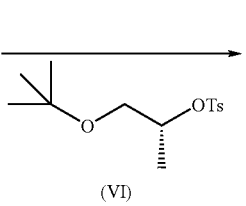
(VI)
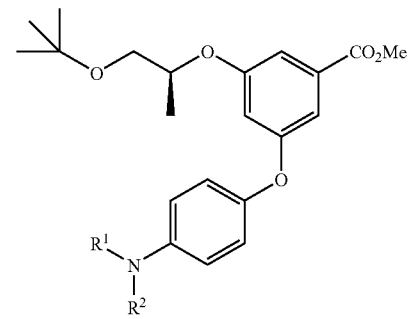

It should be noted that the route illustrated in Scheme 5, although using the same dihydroxymethylbenzoate starting material as the route shown in Scheme 2, advantageously requires fewer steps and fewer protecting groups.

Compounds of formula (III) may be made as illustrated in Scheme 6 (wherein $P^1$ is tert-butyl).

Scheme 6

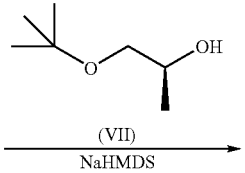
(VII)
NaHMDS

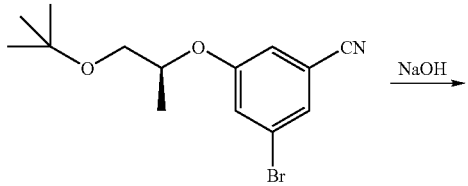
NaOH

-continued

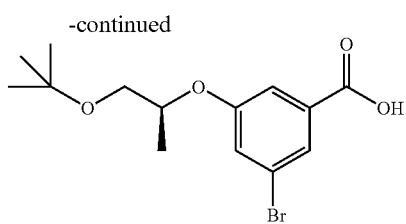

Compounds of formula (VI) and (VII) or analogous compounds with other protecting groups can be made by methods known in the art from the commercially available propanediol starting materials, such as:

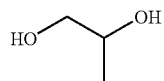

Compounds of formula (IV) and (V) are either commercially available or can be made from commercially available material by processes known in the art. See also for example our patent applications WO2005/080359 and WO2005/080360.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "(1-4C)alkyl" includes methyl, ethyl, propyl, isopropyl and t-butyl. An analogous convention applies to other generic terms.

Suitable examples of rings formed by —NR$^1$R$^2$ include morpholino, piperidinyl, piperazinyl, pyrrolidinyl and azetidinyl. A particular ring formed by —NR$^1$R$^2$ is azetidinyl.

Further suitable examples of rings formed by —NR$^1$R$^2$ include homopiperazinyl, homo-morpholino, homo-thio-morpholino (and versions thereof wherein the sulfur is oxidised to an SO or S(O)$_2$ group) and homo-piperidinyl.

Examples of (1-4C)alkyl include methyl, ethyl, propyl, isopropyl, butyl and tert-butyl.

In a further aspect of the invention, there is provided a compound of formula (I) as hereinbefore defined.

In a further aspect of the invention, there is provided a compound of formula (II) as hereinbefore defined.

Suitable and particular values for R$^1$, R$^2$ and P$^1$ in compounds of formula (I) and (II) have been given hereinbefore.

Particular compounds of formula (I) include:

3-[4-(azetidin-1-ylcarbonyl)phenoxy]-5-[(1S)-2-hydroxy-1-methylethoxy]benzoic acid;

3-[4-(azetidin-1-ylcarbonyl)phenoxy]-5-[(1S)-2-tert-butoxy-1-methylethoxy]benzoic acid;

3-[4-(azetidin-1-ylcarbonyl)phenoxy]-5-[(1S)-2-benzyloxy-1-methylethoxy]benzoic acid;

3-[4-(azetidin-1-ylcarbonyl)phenoxy]-5-[(1S)-2-triphenylmethoxy-1-methylethoxy]benzoic acid;

3-[4-(azetidin-1-ylcarbonyl)phenoxy]-5-[(1S)-2-tetrahydropyran-2-yloxy-1-methylethoxy]benzoic acid.

Particular compounds of formula (II) include

3-[4-(azetidin-1-ylcarbonyl)phenoxy]-5-[(1S)-2-hydroxy-1-methylethoxy]benzoic acid methyl ester;

3-[4-(azetidin-1-ylcarbonyl)phenoxy]-5-[(1S)-2-tert-butoxy-1-methylethoxy]benzoic acid methyl ester;

3-[4-(azetidin-1-ylcarbonyl)phenoxy]-5-[(1S)-2-benzyloxy-1-methylethoxy]benzoic acid methyl ester;

3-[4-(azetidin-1-ylcarbonyl)phenoxy]-5-[(1S)-2-triphenylmethoxy-1-methylethoxy]benzoic acid methyl ester;

3-[4-(azetidin-1-ylcarbonyl)phenoxy]-5-[(1S)-2-tetrahydropyran-2-yloxy-1-methylethoxy]benzoic acid methyl ester.

A particular compound of formula (III) is 3-bromo-5-[(1S)-2-tert-butoxy-1-methylethoxy]benzoic acid.

A particular compound of formula (IV) is 4-(azetidin-1-ylcarbonyl)phenol.

The compounds of formula (I) made by the process of the invention may be reacted to form compounds which are useful as activators of glucokinase (GLK). This activity may be demonstrated by test methods known in the art, for example those given in our patent applications WO 03/015774, WO2005/080359 and WO2005/080360. See also Brocklehurst et al, Diabetes 2004, 53, 535-541.

Compounds of formula (I) may be further elaborated to make compounds of formula (D) as defined hereinbefore. Processes to carry out this conversion are illustrated in Scheme 4 and in the accompanying examples. Suitably, the carboxylic acid of formula (I) may be coupled with a heterocylic amine derivative by using an appropriate coupling reaction, such as a carbodiimide coupling reaction performed with 1-(3-dimethylaminopropyl)-3-ethylcarbodiimide hydrochloride (EDAC) in the presence of dimethylaminopyridine (4-DMAP) in a suitable solvent such as DCM, chloroform or DMF at room temperature; or alternatively with carbonyldiimidazole (CDI) in a suitable solvent such as THF at room temperature; or alternatively using 2-chloro-4,6-dimethoxy-1,3,5-triazine (CDMT) in a suitable solvent such as acetonitrile, for example at 0° C. to room temperature; or by a reaction in which the carboxylic group is activated to an acid chloride by reaction with a suitable reagent, such as oxalyl chloride or 1-chloro-N,N,2-trimethyl-prop-1-en-1-amine in the presence of a suitable solvent such as DCM, and where necessary catalytic amount of DMF. The acid chloride can then be reacted with a compound of formula (VIII) (as defined hereinafter) in the presence of a base, such as triethylamine or pyridine, in a suitable solvent such as DCM or pyridine at a temperature between 0° C. and 80° C.

In a further feature of the invention, there is provided a process for forming a compound of formula (D)

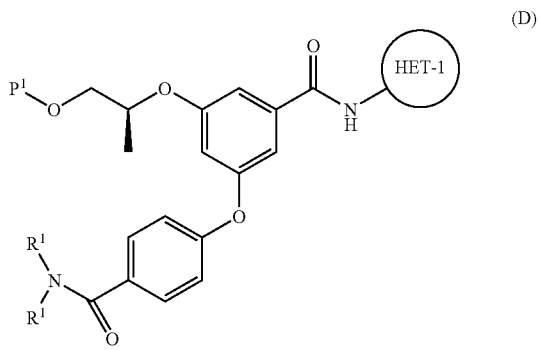

comprising making a compound of formula (I),

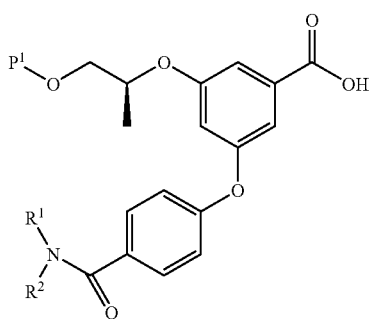

(I)

by either step a):
a) hydrolysis of an ester of formula (II) (wherein R is (1-4C) alkyl);

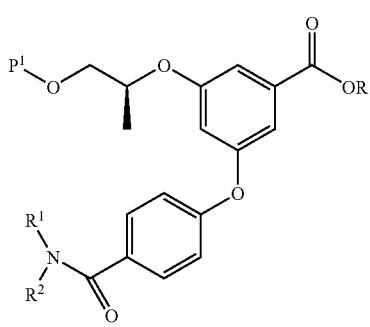

(II)

or step b):
b) reaction of a halo derivative of formula (III) (wherein Hal represents a halogen) with a compound of formula (IV);

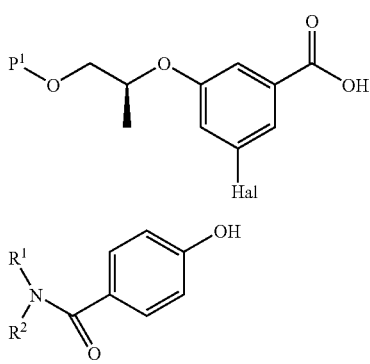

(III)

(IV)

and then
c) reacting the compound of formula (I) with a compound of formula (VIII) to give the compound of formula (D):

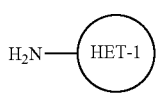

(VIII)

wherein $R^1$ and $R^2$ are independently selected from hydrogen and (1-6C)alkyl, or $R^1$ and $R^1$ together with the nitrogen to which they are attached form a 4- to 7-membered heterocyclic ring, said ring optionally containing 1 further heteroatom selected from O, N and S;
$P^1$ is hydroxy or a hydroxy protecting group;
HET-1 is an optionally substituted 5- or 6-membered, C-linked heteroaryl ring containing a nitrogen atom in the 2-position.

Suitable conditions for steps a) and b) are as hereinbefore described. Suitably step c) is carried out using coupling conditions as hereinbefore described, such as CDI or CDMT. Optionally, when $P^1$ is a hydroxy protecting group, the compound of formula (D) may be deprotected to give the corresponding compound wherein $P^1$ is hydrogen.

For the avoidance of doubt, reference to the group HET-1 containing a nitrogen in the 2-position, is intended to refer to the 2-position relative to the amide nitrogen atom to which the group is attached.

Suitable examples of HET-1 as a 5- or 6-membered, C-linked heteroaryl ring as hereinbefore defined, include thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl.

HET-1 may optionally be substituted with 1 or 2 substituents independently selected from (1-4C)alkyl, halo, hydroxy (1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl and di(1-4C)alkylamino(1-4C)alkyl. Preferably HET-1 is optionally substituted by 1 or 2 halo or (1-4C)alkyl substituents, particularly (1-4C)alkyl.

A preferred value for HET-1 is N-methylpyrazolyl.

In another aspect of the invention, there is provided
i) reaction of a compound of formula (IX) with a compound of formula (X) to give a compound of formula (XI);
ii) reaction of the compound of formula (XI) with a compound of formula (XII) to give a compound of formula (XIII); and optionally
iii) reaction of the compound of formula (XIII) to give a compound of formula (XIV).

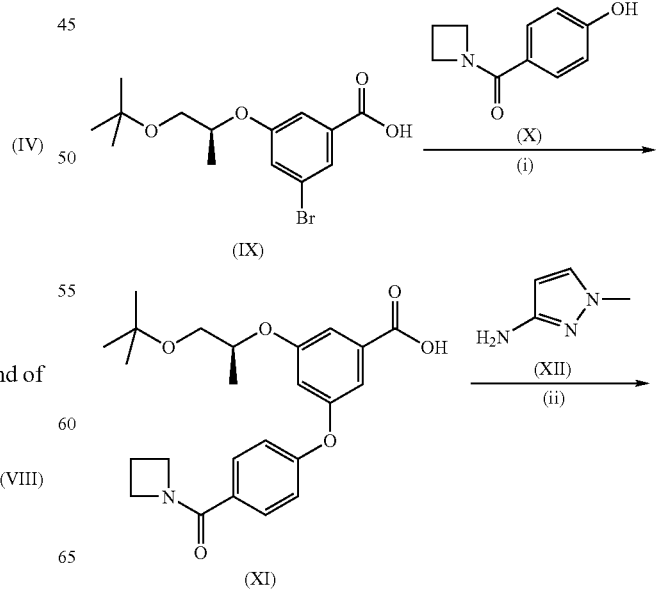

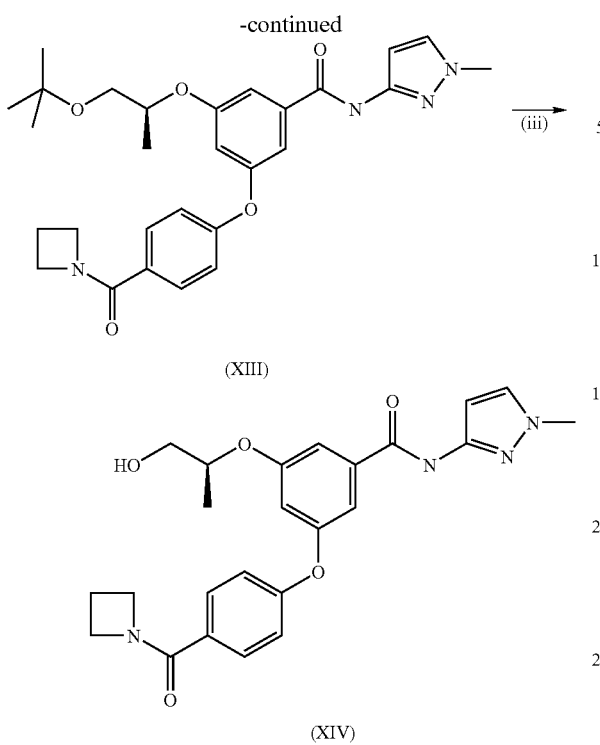

(XIII)

(XIV)

Suitable conditions for step i) are those given for step b) hereinbefore. Suitable conditions for step ii) are those given for step c) hereinbefore. Suitable conditions for step iii) are those described previously for deprotecting $P^1$ as a hydroxy protecting group to give a compound wherein $P^1$ is hydrogen. Further suitable conditions for the each step of the above aspect may be found in the accompanying examples.

In a further aspect of the invention there is provided a compound of formula (I) obtained by the process of the invention. In another aspect of the invention there is provided a compound of formula (I) obtainable by the process of the invention.

It will be appreciated that methods for, for example purification, of the compounds in the Examples below are illustrative and alternatives may be used where the skilled person would deem them appropriate.

The invention will now be illustrated by the following Examples, in which, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis.

ABBREVIATIONS

DCM dichloromethane
DMSO dimethyl sulphoxide
DMF dimethylformamide
HPLC high pressure liquid chromatography
LCMS liquid chromatography/mass spectroscopy
NMR nuclear magnetic resonance spectroscopy
$CDCl_3$ deuterochloroform
MTBE methyltert-butyl ether
THF tetrahydrofuran
NMP N-methylpyrrolidone
TFA trifluoroacetic acid
EtOAc ethyl acetate
$CD_3OD$ perdeuteromethanol
MeOH methanol
RT room temperature

EXAMPLE 1

4-(Azetidin-1-ylcarbonyl)phenol

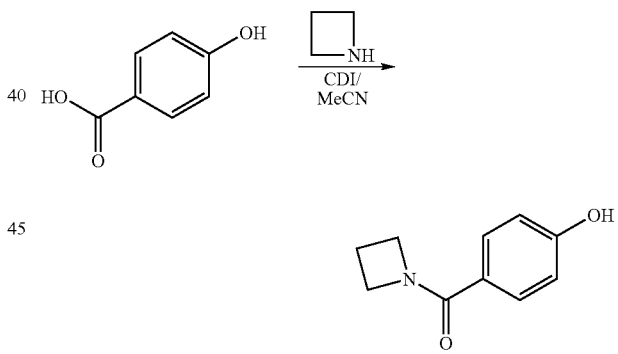

1,1-Carbonyldiimidazole (95.57 mmol; 16.57 g) was charged to a 250 mL round bottomed flask purged with nitrogen, acetonitrile (72 mL) was added, to form a mobile white slurry. 4-Hydroxybenzoic acid (86.88 mol; 12.00 g) was added in portions over 30 minutes to give clear yellow solution, which then became a slurry after approximately 15 minutes. The slurry was heated to 50° C. and azetidine (104.25 mol; 5.95 g) in acetonitrile (10 mL) was added drop wise over 10 minutes. Further azetidine (17.38 mmol; 992.08 mg) was added in acetonitrile (12 mL) and the reaction mixture was heated to 50° C. for a further hour. The precipitated product (10 g, 65% yield) was isolated by filtration and washed with acetonitrile (15 mL) and then dried in a vacuum oven at 40° C.

¹H NMR (400 MHz, d⁶-DMSO) 9.96 (s, 1H), 7.48 (d, 2H), 6.78 (d, 2H), 4.28 (s, 2H), 4.0 (s, 2H), 2.23 (quintet, 2H)

3-Bromo-5-[(1S)-2-tert-butoxy-1-methylethoxy]benzonitrile

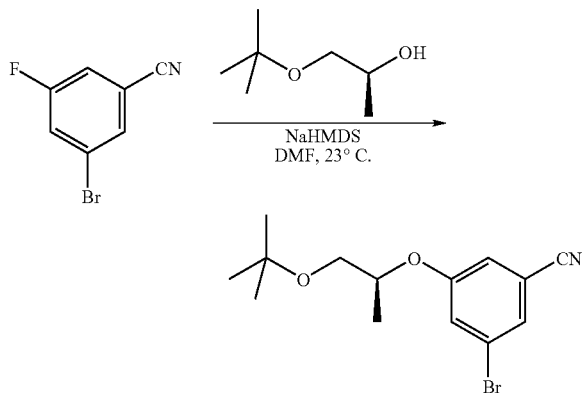

All glassware was oven dried and cooled under nitrogen—inertion was maintained throughout experiment.

To a stirred suspension of sodium bis(trimethylsilyl)amide (74.25 mmol; 14.33 g) in DMF (150 mL) at 23° C. was added (S)-tert-butoxy-2-propanol (74.25 mmoles, 9.82 g) over 15 minutes. A slight exotherm was observed (cold water cooling bath applied). A solution of 3-bromo-5-fluorobenzonitrile (49.50 mmol, 10.0 g) in DMF (40 mL) was added over 15 minutes with cold water bath still present. An exotherm (3° C.) was observed and the mixture turned from yellow to brown. DMF (10 mL) was added and the mixture stirred at ambient temperature for 1 hour. The reaction was quenched by addition of aqueous HCl (2M, 100 mL), maintaining temperature below 25° C. The mixture was diluted with water (200 mL) and extracted with 2:1 EtOAc/MTBE (3×200 mL). The organic layers were combined, washed with water (3×200 mL) and dried over MgSO₄, and the solvent removed in vacuo affording the title compound as an orange oil (17.4 g). Further drying in vacuo at 23° C. gave the title product (15.5 g, ~100%).

¹H NMR: (400 MHz, CDCl₃) δ 7.38-7.35 (m, 1H), 7.34-7.31 (m, 1H), 7.18-7.14 (m, 1H), 4.51-4.41 (m, 1H), 3.53 (dd, 1H), 3.42 (dd, 1H), 1.31 (d, 3H), 1.17 (s, 9H).

3-Bromo-5-[(1S)-2-tert-butoxy-1-methylethoxy]benzoic acid

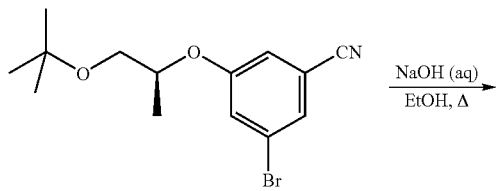

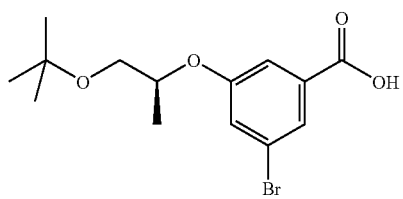

To a stirred solution of 3-bromo-5-[(1S)-2-tert-butoxy-1-methylethoxy]benzonitrile (1.00 equiv, 42.60 mmoles, 13.30 g) in ethanol (135 mL) and water (13.30 mL) was added sodium hydroxide liquor (46/48% w/w, 5213.0 mmol, 12.10 mL, 18.27 g). The resultant yellow solution was heated to reflux for 1 hour and the solvent removed in vacuo to give a wet orange solid. The mixture was partitioned between water (150 mL) and MTBE (100 mL). The coloured upper organic phase contained two layers and was separated from the lower aqueous phase. Note: high solubility of the product sodium salt in the organic phase; only minor loss to the aqueous layer. The organic layers were concentrated to give a gummy orange solid (approx 18 g). The residue was partitioned between aqueous HCl (1M, 200 mL) and MTBE (150 mL). The Layers were separated and the aqueous phase further extracted with MTBE (100 mL). The organic phases were combined, washed with saturated brine (100 mL), dried over MgSO₄, filtered and concentrated in vacuo to give an orange gum (12.85 g), which solidified on standing.

The recovered solid (11.7 g) was stirred in iso-hexane (60 mL) at 23° C. for 35 minutes, isolated by buchner filtration, displacement washed with iso-hexane (2×10 mL) and dried at ambient temperature under nitrogen to give a pale yellow, free flowing solid (8.60 g, 61% yield). The mother liquors were concentrated in vacuo and stirred with iso-hexane (5 mL) for 2 hours. The product was collected by filtration, displacement washed with iso-hexane (2×5 mL) and dried at ambient temperature under nitrogen to give a pale yellow, free flowing solid (1.60 g, 11% yield).

¹H NMR: (400 MHz, CD₃OD) δ$_H$ 7.68 (s, 1H), 7.55 (s, 1H), 7.35 (s, 1H), 4.58-4.48 (m, 1H), 3.55 (dd, 1H), 3.47 (dd, 1H), 1.30 (d, 3H), 1.18 (s, 9H).

3-[4-(Azetidin-1-ylcarbonyl)phenoxy]-5-[(1S)-2-tert-butoxy-1-methylethoxy]benzoic acid

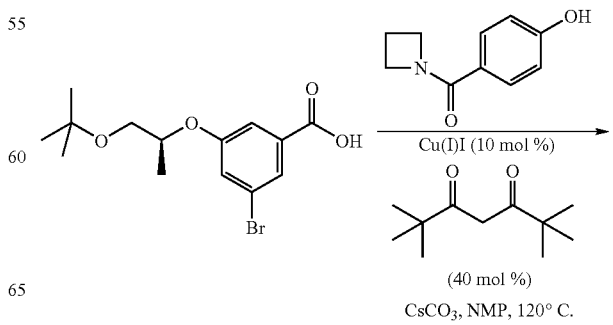

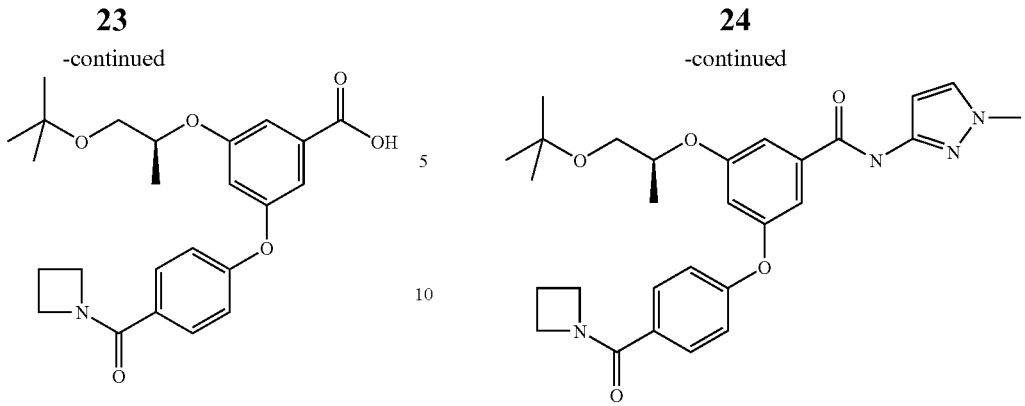

An oven dried, screw capped reaction tube, cooled and purged under nitrogen, containing 3-bromo-5-[(1S)-2-tert-butoxy-1-methylethoxy]benzoic acid (1.8 mmol, 581.3 mg), 4-(azetidin-1-ylcarbonyl)phenol (2.6 mmol, 471.9 mg), cesium carbonate (2.6 mmol, 856.3 mg), copper(I) iodide (163.3 μmol; 31.1 mg), 2,2,6,6-tetramethyl-3,5-heptanedione (702.0 mmol, 146.7 μL) and NMP (5.8 mL) was flushed with nitrogen and sealed. The resultant brown suspension was stirred and heated at 112° C. for 16 hours. The reaction mixture was further heated at 120° C. for 6.5 hours and cooled to ambient temperature. Water was added (10 mL) to dissolve inorganic species and the reaction mixture stirred with MTBE/EtOAc (1:1, 10 mL) for 5 minutes and separated. The aqueous layer was acidified with HCl (2M, 8.8 mmol, 4.4 mL), stirred with MTBE/EtOAc (1:1, 20 mL) for 5 minutes and the layers separated. The organic layer was further washed with aqueous HCl (2M, 8.8 mmol, 4.4 mL) and the layers separated. The organic phase was washed with saturated brine (10 mL), dried over MgSO$_4$, filtered and concentrated in vacuo to give a red gum (767 mg). The residue was purified by column chromatography using EtOAc/DCM/MeOH (10:10:1) to give the title compound as a pale pink solid (493 mg, 66% yield).

$^1$H NMR: (400 MHz, CD$_3$OD) δ$_H$ 7.67 (d, 2H), 7.41 (m, 1H), 7.19 (m, 1H), 7.06 (d, 2H), 6.87 (t, 1H), 4.56-4.45 (m, 1H), 4.41 (t, 2H), 4.19 (t, 2H), 3.55 (dd, 1H), 3.47 (dd, 1H), 2.37 (quintet, 2H), 1.29 (d, 3H), 1.17 (s, 9H).

EXAMPLE 2

3-[4-(Azetidin-1-ylcarbonyl)phenoxy]-5-[(1S)-2-tert-butoxy-1-methylethoxy]-N-(1-methyl-1H-pyrazol-3-yl)benzamide 3-[4-(Azetidin-1-ylcarbonyl)phenoxy]-5-[(1S)-2-tert-butoxy-1-methylethoxy]benzoic acid (853.8 μmol, 365.0 mg) was added portionwise over 30 minutes to a colourless, stirred solution of 1,1'-carbonyldiimidazole (11.1 μmol, 180.3 mg) in acetonitrile (3.5 mL) in an oven dried tube under a nitrogen atmosphere at 25° C. The resultant pink solution was stirred at 25° C. for 35 minutes. The reaction solution was then heated to 50° C., 1-methyl-3-aminopyrazole (1.3 mmol, 130 μL) was added in a single portion and the mixture stirred overnight at temperature. The solvent was removed in vacuo to give a red oil (700 mg). The residue was partioned between MTBE (10 mL) and saturated sodium hydrogen carbonate solution (6 mL). A red oily interface was present. EtOAc (5 mL) was added and the two phase mixture was stirred for 5 minutes and the interface disappeared. The organic phase was further washed with saturated sodium hydrogen carbonate solution (5 mL), water (5 mL), saturated brine (10 mL), and was then dried over MgSO$_4$, filtered and concentrated in vacuo to give a pale yellow/brown foam (385 mg, 89% yield).

$^1$H NMR: (400 MHz, CD$_3$OD) δ$_H$ 7.68 (d, 2H), 7.48 (d, 1H), 7.34 (s, 1H), 7.17 (s, 1H), 7.08 (d, 2H), 6.84 (t, 1H), 6.57 (d, 1H), 4.63-4.49 (m, 1H), 4.41 (t, 2H), 4.19 (t, 2H), 3.81 (s, 3H), 3.56 (dd, 1H), 3.48 (dd, 1H), 2.36 (quintet, 2H), 1.30 (d, 3H), 1.17 (s, 9H).

3-[4-(Azetidin-1-ylcarbonyl)phenoxy]-5-[(1S)-2-hydroxy-1-methylethoxy]-N-(1-methyl-1H-pyrazol-3-yl)benzamide

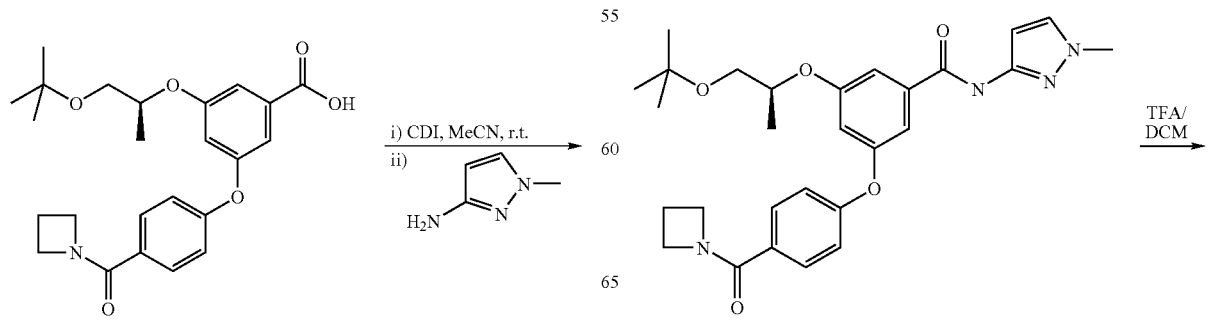

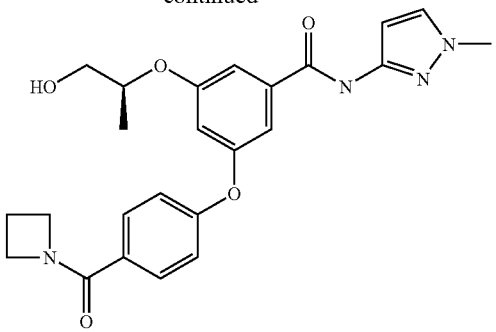

3-[4-(Azetidine-1-carbonyl)-phenoxy]-5-((S)-2-tert-butoxy-1-methyl-ethoxy)-N-(1-methyl-1H-pyrazol-3-yl)-benzamide (101.3 μmol; 51.3 mg) was charged to a small screw capped reaction tube. DCM (500.0 μL) was added the reaction mixture followed by TFA (506.3 μmol; 38.3 μL; 57.7 mg), the reaction mixture was stirred at ambient temperature for 18 hours. HPLC analysis showed no reaction after this time. The reaction mixture was heated to 40° C., extra TFA (506.3 μmol; 38.3 μL; 57.7 mg) was added to the reaction tube and the mixture was held at 40° C. for 18 hours. Water (1 mL) was added to the reaction tube followed by sodium hydroxide (2M) (1.0 mmol; 506.3 μL; 526.6 mg). MTBE (4 mL) was added and the mixture was stirred for 5 minutes. An oily gum had formed which was dissolved by addition of EtOAc (2 mL). The two layers were separated and the upper organic layer was retained, the aqueous was extracted again with EtOAc (2×5 mL). The combined organic layers were washed with saturated brine (5 mL), dried over MgSO$_4$, filtered and concentrated in vacuo to give a colourless oil (35 mg, 75.7% yield).

$^1$H NMR: (400 MHz, CD$_3$OD) δ$_H$ 7.64 (d, 2H), 7.45 (d, 1H), 7.32 (s, 1H), 7.15 (s, 1H), 7.04 (d, 2H), 6.83 (s, 1H), 6.56 (d, 1H), 4.53 (sextet, 1H), 4.37 (t, 2H), 4.15 (t, 2H), 3.77 (s, 3H), 3.64 (d, 2H), 2.32 (quintet, 2H), 1.26 (d, 3H).

EXAMPLE 3

3-[4-(Azetidin-1-ylcarbonyl)phenoxy]-5-[(1S)-2-tert-butoxy-1-methylethoxy]-N-(1-methyl-1H-pyrazol-3-yl)benzamide

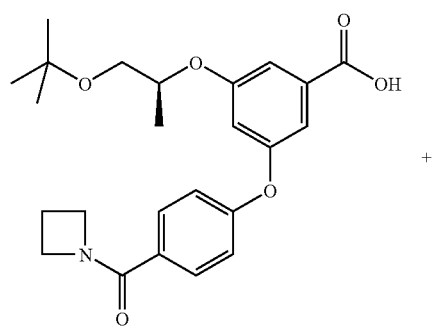

+

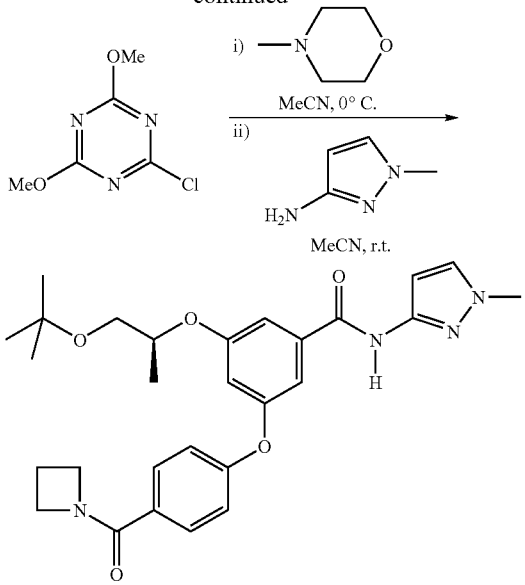

3-[4-(Azetidin-1-ylcarbonyl)phenoxy]-5-[(1S)-2-tert-butoxy-1-methylethoxy]benzoic acid (6.18 mmol, 2.64 g) and acetonitrile (18.5 mL) were charged to a vessel. The contents were stirred and cooled to 0° C. 2-Chloro-4,6-dimethoxy-1,3,5-triazine (6.78 mmol, 1.19 g) was added to the slurry followed by an addition of N-methylmorpholine (8.11 mmol, 0.82 g), added over 20 minutes. The reaction was held for approximately 1 hour at 0° C. and allowed to warm up to ambient. N-methylaminopyrazole (6.79 mmol, 0.66 g) was added over 20 minutes and the reaction held at ambient temperature until the reaction was complete. Water (7 mL) was added to the reaction mixture and the acetonitrile removed by distillation at reduced pressure. Ethyl acetate (32 mL), water (7 mL) and sodium bicarbonate solution (10% by weight, 26 mL) were added to the resultant slurry. The bi-phasic liquor was separated and the ethyl acetate phase sequentially washed with further sodium bicarbonate (10% by weight, 13 mL), water (13 mL), 2M hydrochloric acid (2×13 mL), and then with water (2×13 mL). The washed organic phase was azeodistilled at reduced pressure, removing water and solvent, to give a light brown foam (2.9 g, 90% yield).

$^1$H NMR: (400 MHz, d$_6$-DMSO) δ$_H$ 10.85 (1H, s), 7.65 (2H, d), 7.58 (1H, d), 7.45 (1H, s), 7.21 (1H, s), 7.05 (2H, d), 6.81 (1H, t), 6.54 (1H, d), 4.61 (1H, sextet), 4.30 (2H, br t), 4.02 (2H, m), 3.75 (3H, s), 3.47 (1H, dd), 3.39 (1H, dd), 2.23 (2H, quintet), 1.23 (3H, d), 1.10 (s, 9H).

EXAMPLE 4

3-[4-(Azetidin-1-ylcarbonyl)phenoxy]-5-[(1S)-2-tert-butoxy-1-methylethoxy]benzoic acid 3-Bromo-5-[(1S)-2-tert-butoxy-1-methylethoxy]benzoic acid (9.78 g, 29.51 mmol), 4-(azetidin-1-ylcarbonyl)phenol (7.84 g, 44.70 mmol), cesium carbonate (19.23 g, 59.03 mmol) and NMP (78 mL) were mixed together in a dry reaction flask and agitated overnight under a nitrogen atmosphere. Copper (I) iodide (0.56 g, 2.95 mmol), 2,2,6,6-tetramethylheptane-3,5-dione (2.18 g, 11.81 mmol) and an NMP line wash (20 mL) were added under a nitrogen atmosphere. The reaction mixture was heated to 125° C. for approximately 20 hours.

The reaction mixture was then cooled to 22° C., and diluted with MTBE (59 mL) and water (59 mL). Further 2,2,6,6,-tetramethylheptane-3,5-dione (5.55 g, 29.5 mmol) was added and the upper layer separated off from the reaction mixture. The lower aqueous layer was extracted with MTBE (59 mL) and 2,2,6,6,-tetramethylheptane-3,5-dione (5.55 g, 29.5 mmol) twice more.

The aqueous layer was then acidified using 2M hydrochloric acid (59 mL), and the majority of the mixture extracted into ethyl acetate (98 mL). The aqueous layer was re-extracted with a second smaller portion of ethyl acetate (19.6 mL). The ethyl acetate layers were combined and the residual NMP removed by three water washes (98 mL). Water (98 mL) was then added to the ethyl acetate solution of the product, and potassium carbonate (4.89 g, 35.42 mmol) was added. The lower aqueous phase containing the product was separated off, and the organic layer discarded. Ethyl acetate (98 mL) was added to the aqueous phase followed by 2M hydrochloric acid (37 mL). The layers were separated and the lower aqueous phase was discarded.

Water (98 mL) was added to the ethyl acetate layer, and potassium carbonate (4.89 g, 35.42 mmol) was added. The lower aqueous phase containing the product was separated off, and the organic layer discarded. Ethyl acetate (98 mL) was added to the aqueous phase followed by 2M hydrochloric acid (37 ml). The layers were separated and the lower aqueous phase was discarded.

Water (98 mL) was added to the ethyl acetate layer, and potassium carbonate (4.89 g, 35.42 mmol) was added. The lower aqueous phase containing the product was separated off, and the organic layer discarded. MTBE (98 mL) was added to the aqueous layer. The mixture was warmed to 50° C. and 2M hydrochloric acid (37 mL) was added. The layers were separated and the lower aqueous phase was discarded. The MTBE layer was washed with a small amount of water (20 mL) at 50° C., then was distilled to remove water, passed through a fine filter, cooled to 22° C. and seeded. Isohexane (147 mL) was added to the crystalline slurry. The mixture was cooled to −10° C., filtered, and washed with 1:2 MTBE: isohexane (29 mL). The isolated product was dried in the vacuum oven at 50° C. (yield at 100% strength=58.4%).

The invention claimed is:

1. A process for making a compound of formula (I),

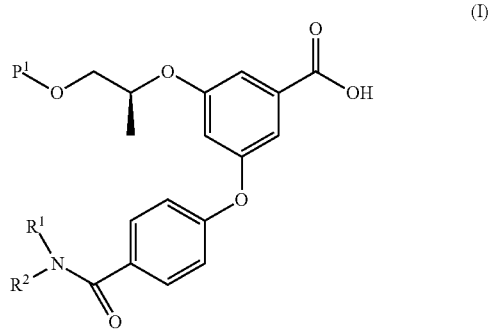

(I)

said process comprising either:
a) hydrolyzing an ester of formula (II) wherein R is (1-4C) alkyl;

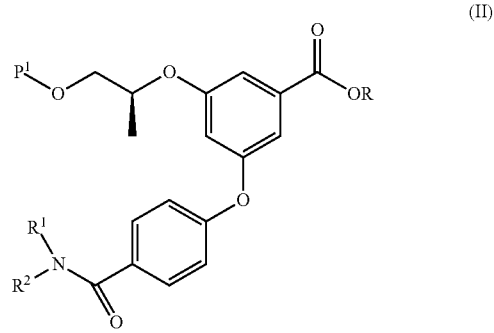

(II)

or
b) reacting a halo derivative of formula (III) wherein Hal represents a halogen with a compound of formula (IV);

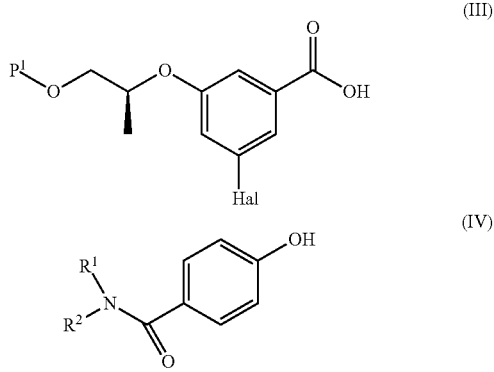

(III)

(IV)

wherein in compounds of formula (I) to (IV), $R^1$ and $R^2$ are independently selected from hydrogen and (1-6C)alkyl, or $R^1$ and $R^2$ together with the nitrogen to which they are attached form a 4-to 7-membered heterocyclic ring, said ring optionally containing 1 further heteroatom selected from O, N and S; and
$P^1$ is hydrogen or a hydroxy protecting group.

2. The process as claimed in claim 1, wherein the compound of formula (I) is made by process b).

3. The process as claimed in claim 1, wherein $P^1$ is t-butyl.

4. The process as claimed in claim 1 wherein $R^1$ and $R^2$ together with the nitrogen to which they are attached form a 4-to 7-membered heterocyclic ring.

5. The process as claimed in claim 4 wherein $R^1$ and $R^2$ together with the nitrogen to which they are attached form an azetidinyl ring.

6. The process as claimed in claim 1 wherein process b) is carried out in the presence of copper(I) iodide or copper(I) oxide as catalyst.

7. The process as claimed in claim 1 wherein process b) is carried out in the presence of 2,2,6,6-tetramethylheptane-3, 5-dione.

8. The process as claimed in claim 1 wherein process b) is carried out in NMP or benzonitrile.

9. The process as claimed in claim 1, wherein the compound of formula (I) is then reacted with a compound of formula (VIII)

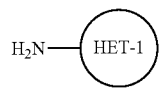

(VIII)

to form a compound of formula (D), wherein HET-1 is an optionally substituted 5- or 6-membered, C-linked heteroaryl ring containing a nitrogen atom in the 2-position

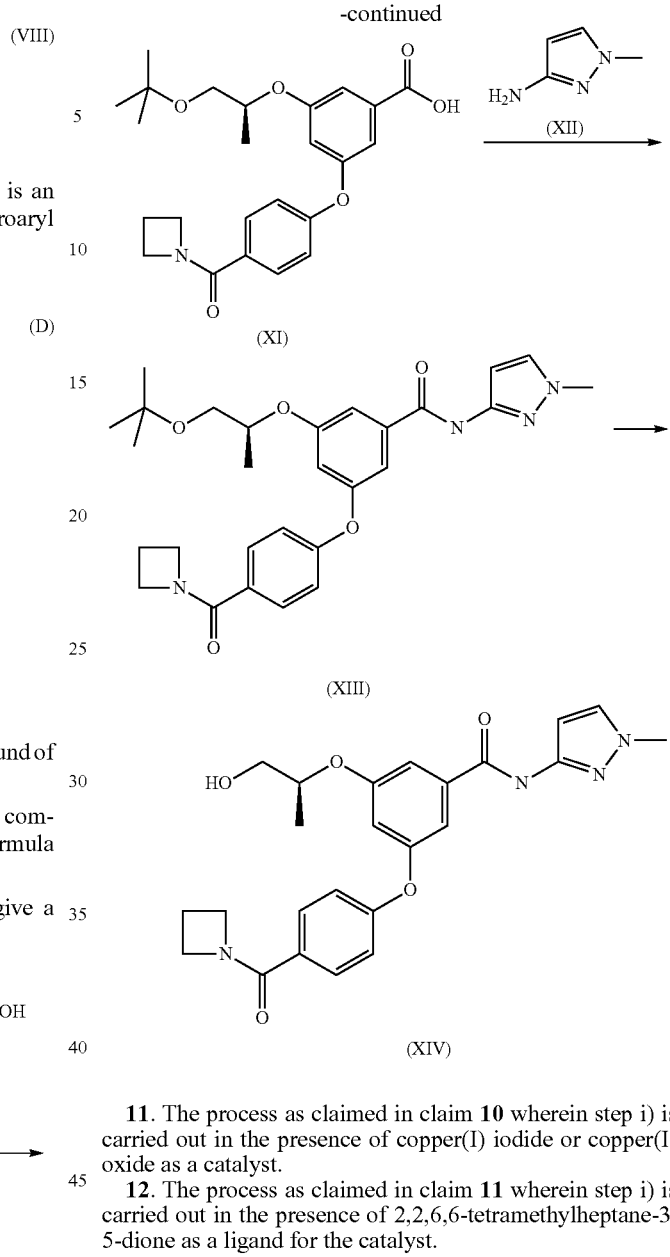

10. The process as claimed in claim 9 comprising:

i) reacting a compound of formula (IX) with a compound of formula (X) to give a compound of formula (XI);

ii) reacting the compound of formula (XI) with a compound of formula (XII) to give a compound of formula (XIII); and optionally iii) reacting the compound of formula (XIII) to give a compound of formula (XIV)

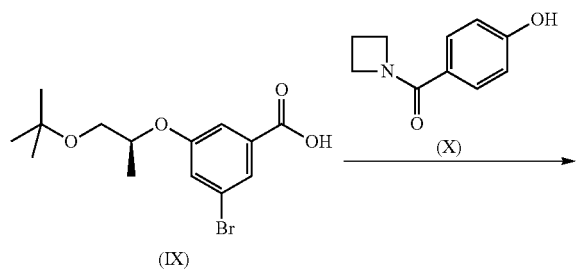

11. The process as claimed in claim 10 wherein step i) is carried out in the presence of copper(I) iodide or copper(I) oxide as a catalyst.

12. The process as claimed in claim 11 wherein step i) is carried out in the presence of 2,2,6,6-tetramethylheptane-3,5-dione as a ligand for the catalyst.

* * * * *